(12) United States Patent
Key et al.

(10) Patent No.: US 7,388,204 B2
(45) Date of Patent: Jun. 17, 2008

(54) APPARATUS AND METHOD FOR ANALYZING RELATIVE OUTWARD FLOW CHARACTERIZATIONS OF FABRICATED FEATURES

(75) Inventors: Douglas E. Key, Cleves, OH (US); Beau Easton, Walton, KY (US)

(73) Assignee: Meyer Tool, Inc., Cincinnati, OH (US)

( * ) Notice: Subject to any disclaimer, the term of this patent is extended or adjusted under 35 U.S.C. 154(b) by 168 days.

(21) Appl. No.: 11/424,084

(22) Filed: Jun. 14, 2006

(65) Prior Publication Data

US 2007/0290134 A1    Dec. 20, 2007

(51) Int. Cl.
*G01J 5/02* (2006.01)
(52) U.S. Cl. .................... 250/340; 250/339.03
(58) Field of Classification Search ............... 250/340, 250/339.03
See application file for complete search history.

(56) References Cited

U.S. PATENT DOCUMENTS

| | | | |
|---|---|---|---|
| 3,566,669 | A |   | 3/1971 | Lawrence et al. |
| 4,644,162 | A |   | 2/1987 | Bantel et al. |
| 5,054,087 | A |   | 10/1991 | Carbon et al. |
| 5,111,046 | A | * | 5/1992 | Bantel .................... 250/330 |
| 5,125,035 | A |   | 6/1992 | McCarthy et al. |
| 5,168,747 | A | * | 12/1992 | Weaver et al. ............ 73/40.7 |
| 6,367,968 | B1 |   | 4/2002 | Ringermacher et al. |
| 6,367,969 | B1 |   | 4/2002 | Ringermacher et al. |
| 6,394,646 | B1 |   | 5/2002 | Ringermacher et al. |
| 6,422,743 | B1 |   | 7/2002 | Nirmalan et al. |
| 6,570,175 | B2 | * | 5/2003 | Bales et al. ............... 250/559.4 |
| 6,585,408 | B2 |   | 7/2003 | El-Gabry et al. |
| 6,711,506 | B2 |   | 3/2004 | Bales et al. |
| 6,732,582 | B2 |   | 5/2004 | Bunker et al. |
| 6,750,454 | B2 |   | 6/2004 | Brown et al. |
| 6,804,622 | B2 |   | 10/2004 | Bunker et al. |
| 6,909,800 | B2 |   | 6/2005 | Vaidyanathan |
| 2003/0128736 | A1 | * | 7/2003 | Dalio et al. .............. 374/141 |

OTHER PUBLICATIONS

Journal of Turbomachinery, A Transient Infrared Thermography Method for Simultaneous Film Cooling Effectivenes and Heat Transfer Coefficient Measurements from a Single Test, Oct. 2004, vol. 126, Ekkad et al.

(Continued)

*Primary Examiner*—David P. Porta
*Assistant Examiner*—Mindy Vu
(74) *Attorney, Agent, or Firm*—Wood, Herron & Evans, LLP (57) ABSTRACT

An apparatus and method for characterizing gas flow through features fabricated in a hollow part. A pressurized gas is applied to an interior of the part, and this gas pressure flows outward through features fabricated in the part. At the same time, a stabilizing pressurized gas is applied to an exterior part skin; and the stabilizing gas has a controlled temperature differential from the gas applied to the part interior. An infrared signature of escaping gas and the surrounding part skin is analyzed by a classification method. Analysis of this infrared signature classifies the relative flow rate, size and position of the feature fabricated in the part.

24 Claims, 7 Drawing Sheets

OTHER PUBLICATIONS

InfraMation, Challanges in Infrared Imaging: Low Emissivities of Hot Gases, Metals, and Metallic Cavaties, InfraMation 2004 Proceedings, 10 Pages, Vollmer et al.

Space Nanotechnology Laboratory, Massachusetts Institute of Technology, Fun with the Shack-Hartmann, Aug. 15, 2003, 2 Pages, Andrew Lapsa.

S. V. Ekkad et al., A Transient Infrared Thermography Method for Simultaneous Film Cooling Effectiveness and Heat Transfer Coefficient Measurements From a Single Test, Journal of Turbomachinery, Oct. 2004, vol. 126, pp. 597-603, ASME, USA.

M. Vollmer et al., Challenges in Infrared Imaging: Low Emissivities of Hot Gases, Metals, and Metallic Cavities, InfraMation 2004 Proceedings, Jul. 27, 2004, 10 pages.

R. D. Rosemau et al., Aircraft Engine Blade Cooling Holes Detection and Classification from Infrared Images, Proceedings of the SPIE, Mar. 1999, vol. 3588, pp. 85-93.

A. Lapsa, Fun With The Shack-Hartmann, Space Nanotechnology Laboratory, Massachusetts Institute of Technology, Aug. 15, 2003, 2 pages.

* cited by examiner

◍ = skin point
⊖ = hole point
$X_n, Y_n$ = point of interest

| $X_{n-1}Y_{n-1}$ | $X_nY_{n-1}$ | $X_{n+1}Y_{n-1}$ |
| --- | --- | --- |
| $X_{n-1}Y_n$ | $X_nY_n$ | $X_{n+1}Y_n$ |
| $X_{n-1}Y_{n+1}$ | $X_nY_{n+1}$ | $X_{n+1}Y_{n+1}$ |

APPARATUS AND METHOD FOR ANALYZING RELATIVE OUTWARD FLOW CHARACTERIZATIONS OF FABRICATED FEATURES

FIELD OF THE INVENTION

The present invention relates to manufacturing gas turbine engine components and, more particularly, to inspecting complex cooling holes through a surface of a gas turbine engine component.

BACKGROUND OF THE INVENTION

During operation, gas turbine engines, whether used for flight or stationary power generation, develop extremely high temperature and high velocity gases in a combustor portion of the engine. These gases are ducted on blades of a turbine rotor to cause rotation of the rotor and are redirected by the stator vanes onto additional rotor blades to produce more work. Because of the high heat of the gases, it is desirable to cool the blades and vanes to prevent damage and, to extend the useful life of, these engine components. It is known in the art that a turbine component such as that shown in FIG. 8 can be cooled by film cooling that is provided by a plurality of fabricated features, for example, cooling holes.

Figure 8:
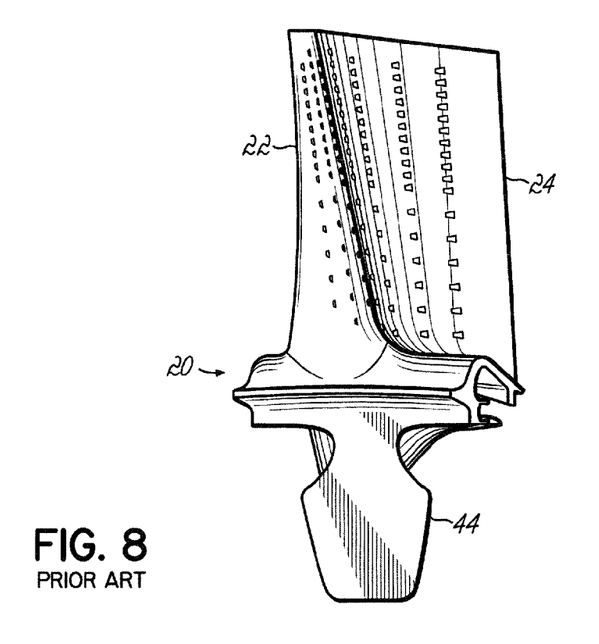
FIG. 8 is a partial perspective view of an example of a known turbine component that utilizes rows of features or cooling holes that must be inspected using the embodiments of FIGS. 1, 2, 3 and 6.

A commonly used method of cooling a turbine component 20 is to duct cooling air through internal passages and then vent the cooling air through a plurality of cooling holes 22. This air cools internal surfaces of the component by convection and cools the components outer surfaces by film cooling. The cooling holes 22 are typically formed along a line generally parallel to, and a selected distance from, a trailing edge 24 of the component to provide a film of cooling air over a surface of the component when the cooling holes discharge air during engine operation. Other rows or arrays of cooling holes or vents may be formed in the blade and vane components of a rotor or stator of a turbine depending upon design constraints.

Figure 9:
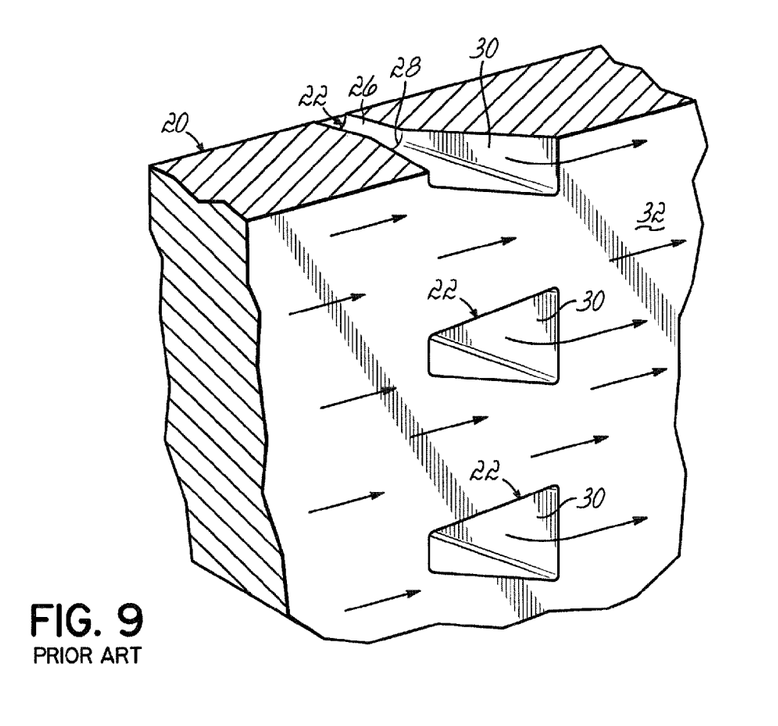
FIG. 9 is a partial perspective and cross-sectional view of a cooling hole in the turbine component illustrated in FIG. 8.

To facilitate the distribution of the cooling air substantially completely over the convex and concave surfaces of the blade airfoil or platform, as shown in FIG. 9, the upstream end of each cooling hole 22 has a generally cylindrical, inlet portion 26 that extends from a location 28 inside of a wall of the component 20. At the location 28, the cooling hole 22 then flares or diverges to provide a discharge portion 30 that terminates on an exterior surface 32 of the component 20 to be cooled by the air flow. The shape of the discharge end functions as a diffuser to reduce the velocity of the cooling airstreams being discharged from the cooling holes 22. The lower velocity cooling airstreams are more inclined to cling to the surface 32 for improved cooling. High quality cooling holes 22 with diffusers 30 provide superior performance but are costly and difficult to manufacture.

After the cooling holes have been manufactured, it is necessary to inspect each of the holes to determine whether it exists and is properly formed as a complex hole. One method of inspection is a manual method in which an inspector is provided with a drawing of the desired hole pattern and a pin. The inspector first confirms that a hole exists at each location identified by the pattern; and then, the inspector inserts the pin through each of the holes to determine whether the hole is properly drilled as a through-hole. As can be appreciated, such an inspection process is highly repetitive, tedious and stressful for the inspector and, in addition, is expensive and inefficient for the manufacturer of the turbine component.

Other known hole inspection processes are automated and utilize a laser or a flow of fluid through the holes. The flowing fluid used most commonly is either air or water. In the case of air, the mass of air flowing through a feature can be measured. With water, a visual signal of a flow pattern is possible. These methods need a human visual check or physical measurement of a single feature to characterize its flow condition, All of these known methods are time-consuming and rely on human intervention to perform the characterization which leads to errors.

Thus, there is a need for an inspection apparatus and process that can automatically inspect and identify qualitative characteristics of complex cooling features in gas turbine components faster, more precisely and less expensively than known inspection apparatus and processes.

SUMMARY OF THE INVENTION

The present invention provides an inspection apparatus and process that accurately and quickly determine the flow characteristics of cooling features fabricated in gas turbine blades. With the inspection apparatus and process of the present invention, the flow characteristics are easy to interpret; and thus, the inspection apparatus and process are faster, more error-free and less expensive than known tactile and visual inspection processes. The inspection apparatus of the present invention provides an automatic process and thus, removes the chance of human error. Therefore, the inspection apparatus of the present invention is especially useful for inspecting a presence and quality of a large number of complex cooling holes in gas turbine component.

These and other objects and advantages of the present invention will become more readily apparent during the following detailed description taken in conjunction with the drawings herein.

DETAILED DESCRIPTION OF THE INVENTION

Figure 1:
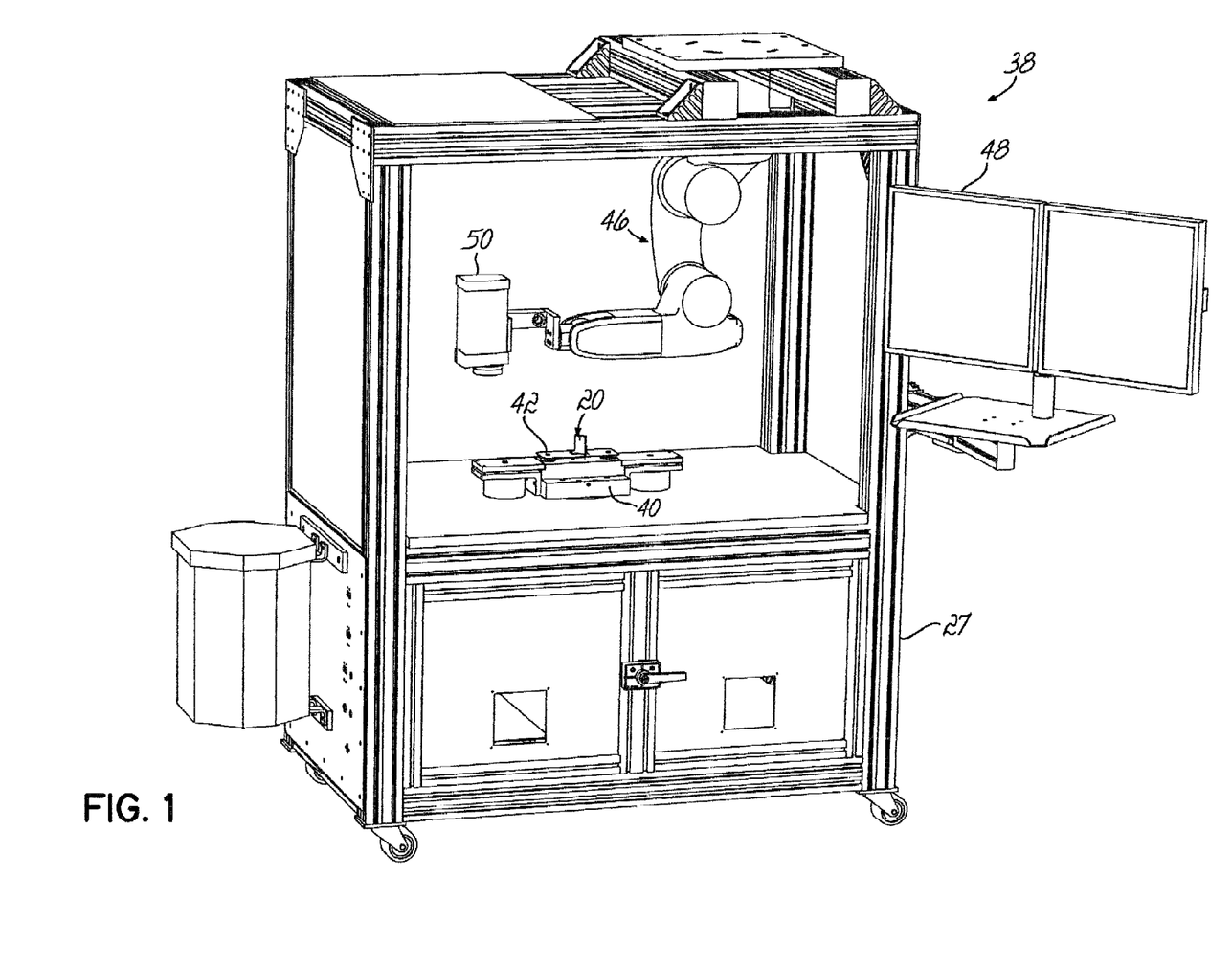
FIG. 1 is a perspective view of a first exemplary embodiment of an automated inspection system for inspecting a complex feature fabricated in a part in accordance with the principles of the present invention.
Figure 2:
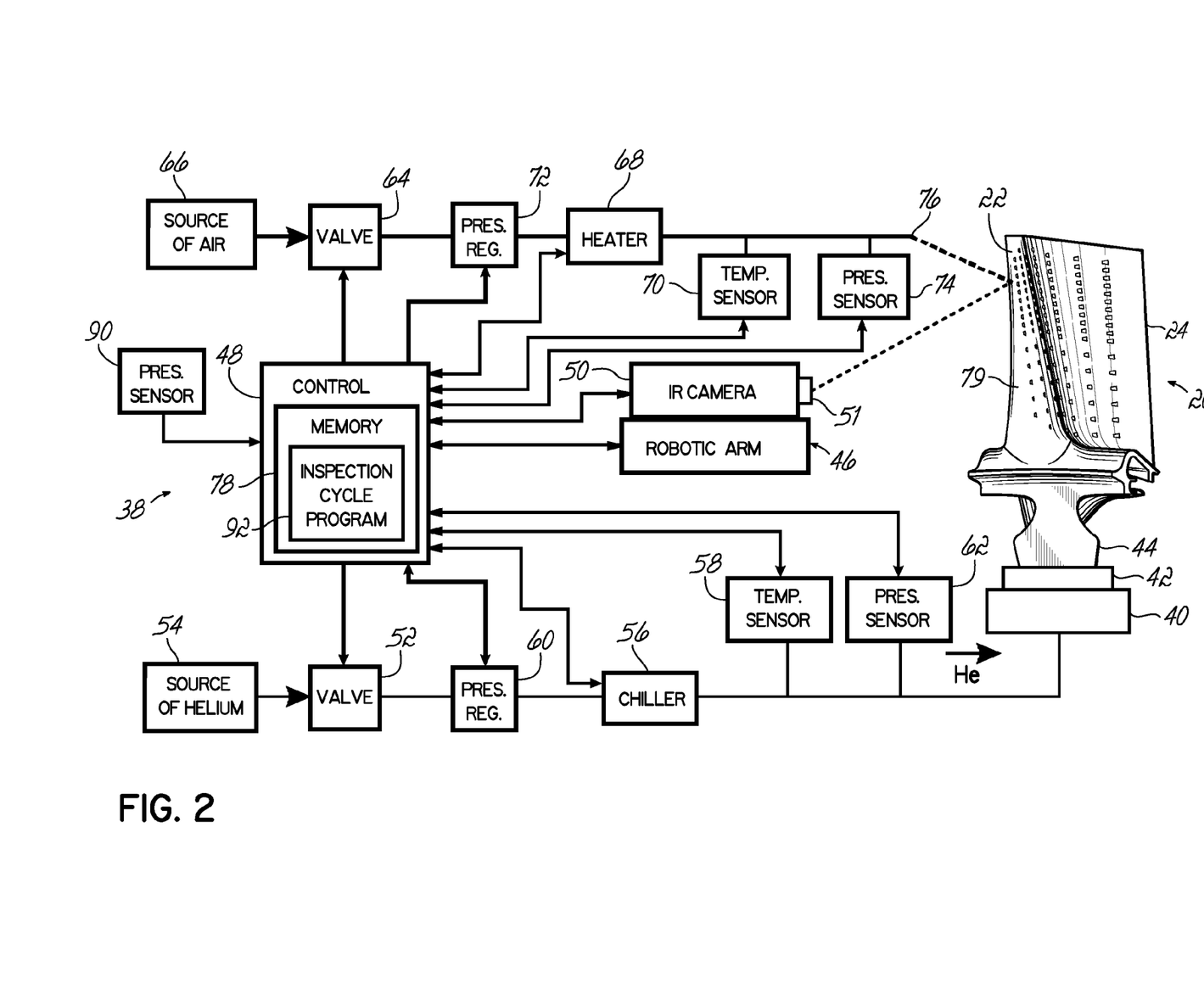
FIG. 2 is an overall schematic diagram of the first exemplary embodiment shown in FIG. 1.

Referring to FIGS. 1 and 2, one example of a feature inspection system 38 is used to inspect fabricated features in a part, for example, air cooling holes 22 in a known turbine blade 20 as described with respect to FIGS. 8 and 9. The blade 20 is supported in a holding fixture 40; and a gas tight seal 42, for example, a molded urethane seal, is formed around an inlet opening at a base 44 of the blade 20. A robotic arm 46 is mounted in a cabinet 27 and is controlled by a programmable control 48 also mounted on the cabinet 27. The robotic arm 46 is operable to position an infrared (IR) radiometer or camera 50 with respect to the blade 20. In one exemplary embodiment, the robotic arm 46 is mounted upside-down above the blade 20, so that the robotic arm 46 can be moved to different positions and orientations that permit the IR camera 50 to provide thermal images of all of the fabricated blade features 22 to be inspected. The robotic arm 46 may be one of several commercially available six-axes robot arms, for example, a six-axes robot arm commercially available from DENSO Robotics of Long Beach, Calif. The IR camera 50 is an uncooled IR detector array consisting of 76,800 micro bolometer elements arranged in a pattern that is 320 elements wide by 240 elements high. The IR camera 50 is capable of detecting electromagnetic energy in the range of 7.5-13 micrometers and may be one of several commercially available cameras such as those available from FLIR Systems, Inc. of Wilsonville, Oreg.

Figure 2A:
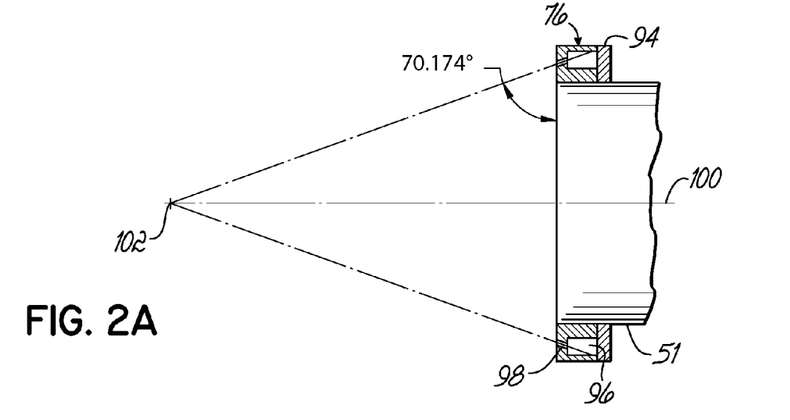
FIG. 2A is a cross-sectional view of an exemplary embodiment of an annular gas discharge nozzle in accordance with the principles of the present invention.

In a feature inspection cycle, the IR camera is positioned at a desired position and orientation with respect to the blade; and the control 48 commands a first valve 64 to open, which allows air from a source of pressurized air 66 to enter a heater 68. The control 48 is also electrically connected to the heater 68 and a first temperature sensor 70 providing a first temperature feedback signal. The control 48 uses the first temperature feedback signal and a known PID control to operate the heater 68 and bring the air temperature to a range of about 70-315 degrees Fahrenheit. A first gas pressure regulator 72 is electrically connected to, and operable by, the control 48 to provide the air at a pressure in a range of about 0.05-3.0 pound(s) per square inch gauge ("PSIG"). This warmer air passes through a nozzle 76 and is applied over an area of a blade outer surface or skin 79 that surrounds the various features 22 being inspected. The nozzle 76 may simply be an open end of a tube positioned adjacent the camera lens 51 and directed toward one or more features being captured by the IR camera 50. In an alternative exemplary embodiment shown in FIG. 2A, the nozzle 76 may be an annular piece 94 ring sized to be mounted around an IR camera lens 51. An annular gas passage 96 intersects a number of angled gas discharge passages 98 located circumferentially around the annular piece 94 and hence, the IR camera lens 51. The gas discharge passages 98 may be angled to intersect a centerline 100 at generally a common point 102, and thus, the discharge passages 98 are angled or directed toward the one or more features to be captured by the IR camera 50.

Simultaneously with opening the first valve 64, the control 48 commands a second valve 52 to open, which allows a helium gas from a source of helium gas 54 to enter a chiller 56. The control 48 is also electrically connected to the chiller 56 and a second temperature sensor 58 providing a second temperature feedback signal. The control 48 uses the second temperature feedback signal and a known PID control to operate the chiller 56 and bring the air to a temperature in a range of about 25-70 degrees Fahrenheit. A second gas pressure regulator 60 is electrically connected to, and operable by, the control 48 to maintain the helium at a pressure in a range of about 0.1-35 PSIG. The chilled and pressurized helium gas is then applied through the fixture 40 and into an interior cavity through an opening at the base 44 of the blade 20 and allowed to escape through the various features 22 that are being inspected.

Figure 3:
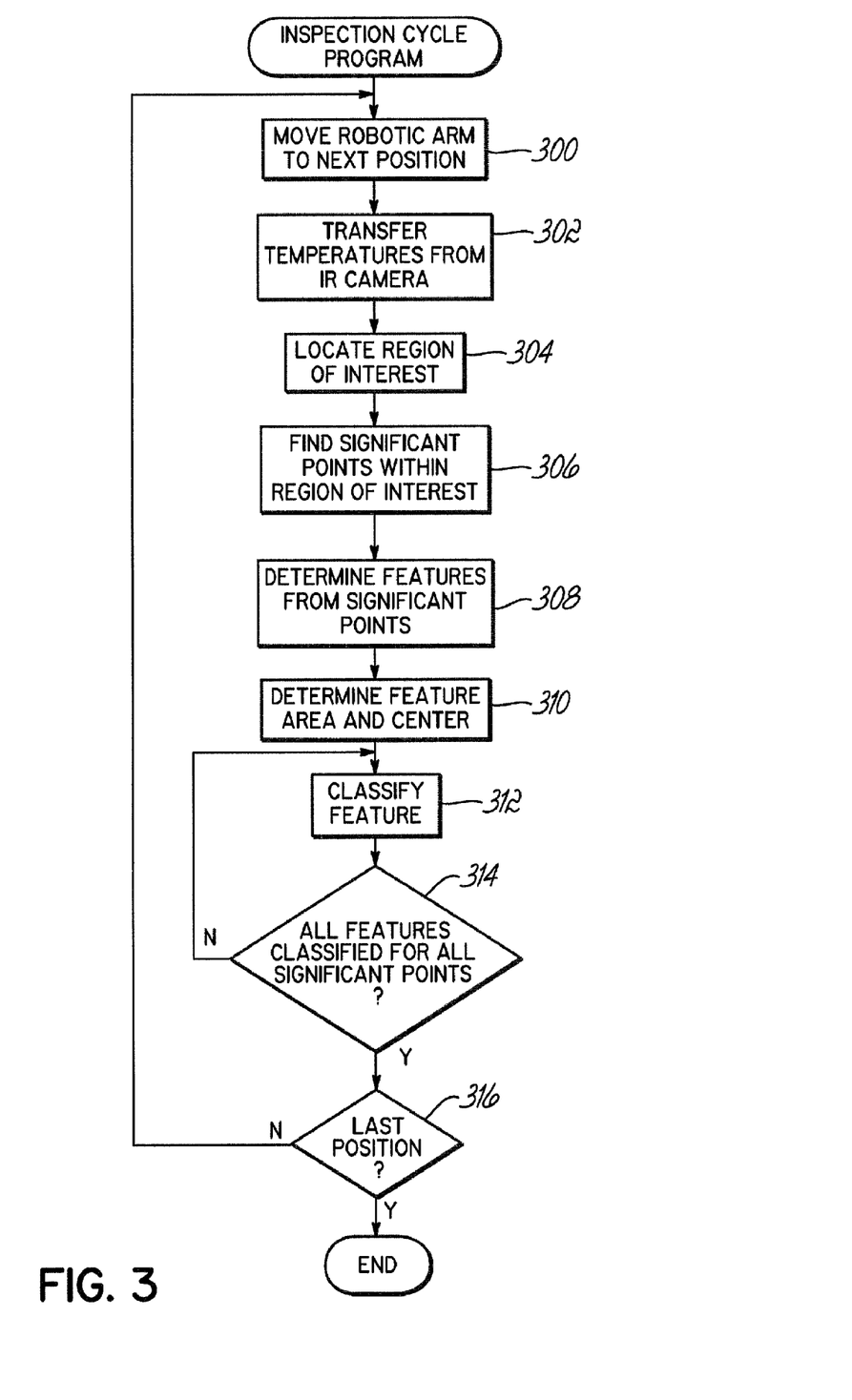
FIG. 3 is a flowchart of an exemplary embodiment of a process for analyzing a raw infrared image using the embodiments of FIGS. 1, 2 and 7.

An initial pre-inspection cycle in a range of about 1-30 seconds is used to purge air from an interior of the blade 20, and the blade 20 is brought to a desired temperature. A control memory 76 stores a hole inspection application program 92 that is operable to inspect the blade features 22 with the IR camera 50 and analyze detected temperatures to identify a feature present, partial feature present or an absence of a feature. The general process executed by the application program 92 is shown in FIG. 3. The control 48 first, at 300, commands the robotic arm to move the IR camera 50 to a first position and orientation with respect to the blade 20. The IR camera 50 is triggered by the control 48 to capture a raw image in an X-Y pattern. The X-Y pattern is a grid of 320 temperatures in the X-axis and 240 temperatures in the Y-axis, for total of 76,800 floating-point temperatures. In this exemplary embodiment, the IR camera 50 is operable to convert the X-Y temperature grid pattern to corresponding digital signals and store them in memory 78.

The control 48 then, at 302, commands a transfer of the temperature grid pattern from the IR camera 50 to the control memory 78. Next, at 304, the entire temperature grid pattern is first analyzed to locate a first region of interest. As will subsequently be described, a region of interest is one or more of the features 22 that have been previously identified in a setup cycle. Therefore, for each programmed IR camera position, one or more regions of interest are stored in the memory 78; and a region can be imposed on, or identified within, the stored X-Y temperature grid pattern.

Figure 4:
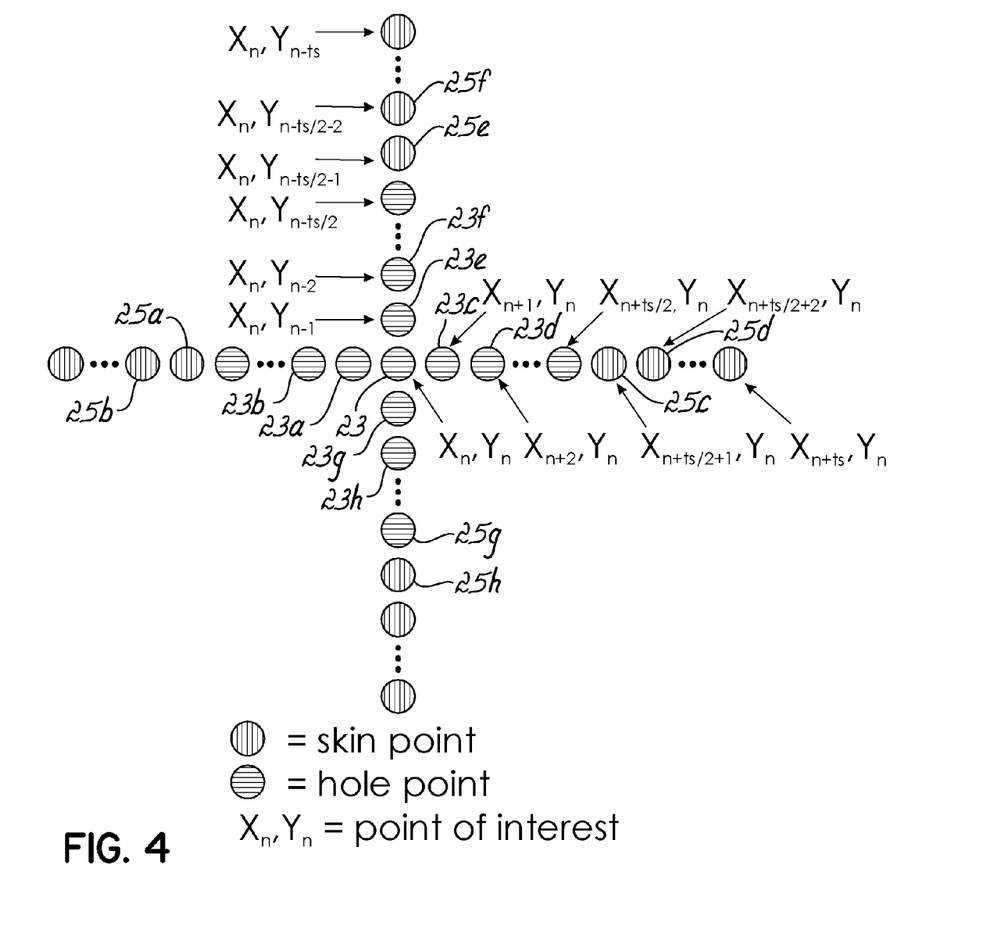
FIG. 4 is an exemplary representation of a point summing cross pattern used in a significant point algorithm with the process shown in FIG. 3.

Thereafter, at 306, a "significant point" detection process begins within a chosen region of interest; and the significant point detection process is used to analyze each X-Y temperature point in the grid pattern of a region of interest. The analysis of each X-Y temperature point begins by summing a first X-Y temperature point with points directly next to it in a first cross pattern to determine an average temperature. A cross pattern size, that is, the number of points to be summed in the four directions from the first point, is determined by a selected target size setting of even numbers in a range of about 2-20 points. The cross pattern size is chosen during the setup cycle as will be described. An example of a point summing cross pattern is shown in FIG. 4. If the temperature point 23 being analyzed and the selected target size is two, then an average value of the temperature points 23-23$h$ is determined using Equation 1 below. Equation 1 is a general mathematical expression or algorithm for determining an average temperature in the first cross pattern, and its result is used as a hole area temperature baseline.

$$\overline{\text{hole}} = \frac{\sum_{i=n-\frac{t_s}{2}}^{i=n+\frac{t_s}{2}} X_i Y_n + \sum_{i=n-\frac{t_s}{2}}^{i=n+\frac{t_s}{2}} X_n Y_i}{2t_s + 2} \quad \text{(Eq. 1)}$$

Where
 $t_s$=target size setting
 n=temperature array index

Next, as further shown in FIG. 4, X-Y temperature points in a second cross pattern beyond the first cross pattern are used in a similar fashion to determine temperature baseline of the surrounding skin area 79. The skin area region represented by a second cross pattern size is also defined by a target size setting of even numbers in a range of about 2-20 points. Continuing with the above example in FIG. 4, for the temperature point 23, if the selected target size is two, then an average value of the temperature points 25a-25h is determined using Equation 2 below. Equation 2 is a general mathematical expression or algorithm for determining an average temperature in the second cross pattern beyond the first cross pattern, and its result is used as a skin area temperature baseline.

$$\overline{\text{skin}} = \frac{\sum_{i=n-t_s}^{i=n-\frac{t_s}{2}-1} X_i Y_n + \sum_{i=n+\frac{t_s}{2}+1}^{i=n+t_s} X_i Y_n + \sum_{i=n-t_s}^{i=n-\frac{t_s}{2}-1} X_n Y_i + \sum_{i=n+\frac{t_s}{2}+1}^{i=n+t_s} X_n Y_i}{2t_s} \quad \text{Eq. 2}$$

Where
 $t_s$=target size setting
 n=temperature array index

Thereafter, a difference between the average skin and hole temperatures is determined using Equation 3a below and compared to a selectable threshold setting in a range of about 0.01-10.

$$\Delta\text{temp} = \overline{\text{skin}} - \overline{\text{hole}} \quad \text{(Eq. 3a)}$$

If the temperature difference between the average skin and hole temperatures is determined to be less than a selected temperature threshold or reference value, then the Xn-Yn temperature point being analyzed is considered not to be significant. In the example of FIG. 4, if the temperature difference using the temperature point 23 is less than the temperature threshold, the temperature point 23 is not considered to be associated with a blade feature 22. The process then repeats the above analysis with the next X-Y temperature point in the X-Y temperature grid.

However, if the average skin and hole temperatures of any X-Y temperature point is greater than the temperature threshold, that X-Y temperature point is considered to represent a temperature point associated with a feature and is stored in the memory 78 as a significant point in an array of significant points. The above process is repeated for all of the points in the region of interest, and the output of this algorithm is an array of significant points. The temperature threshold or reference temperature is determined during the setup process.

Figure 5:
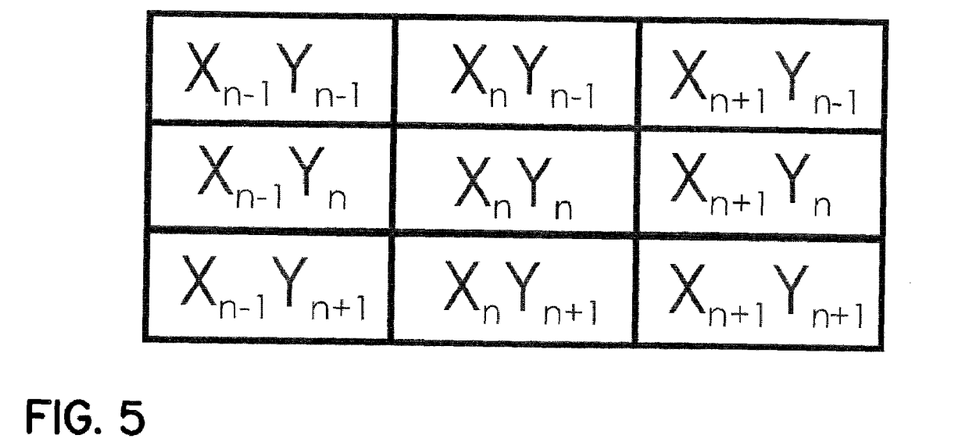
FIG. 5 is a representation of eight-border coordinates used to determine a feature using the process of FIG. 3.

The control 48 is operable, at 308, to identify the various features by detecting all significant points that share a common border. If a significant point is bordered by another significant point, these points are grouped to form a detected feature. The algorithm used for detection is an eight cell test as shown in FIG. 5. For a selected significant point, each of the coordinates for the eight bordering points is tested for its existence in the array of significant points. Bordering points that are found are deleted from the significant point array and stored along with an associated center point as a detected feature in a feature array in the memory 78. This process continues until no further bordering points are found. Thus, each feature identified in the feature array is defined by a center point and eight bordering points. The control 48 repeats the above process until all significant points have been tested.

The center coordinates of each detected feature are determined by the control 48, at 310, using Equations 4 and 5 below. The X center point determined by Equation 4 and the Y center point determined by Equation 5 are each found by dividing a sum of all respective axis points by an area value and adding one as a bias. This area value, A, is used for classification of the feature.

$$X_{center} = \frac{\sum X}{A} + 1 \quad \text{(Eq. 4)}$$

$$Y_{center} = \frac{\sum Y}{A} + 1 \quad \text{(Eq. 5)}$$

Figure 6:
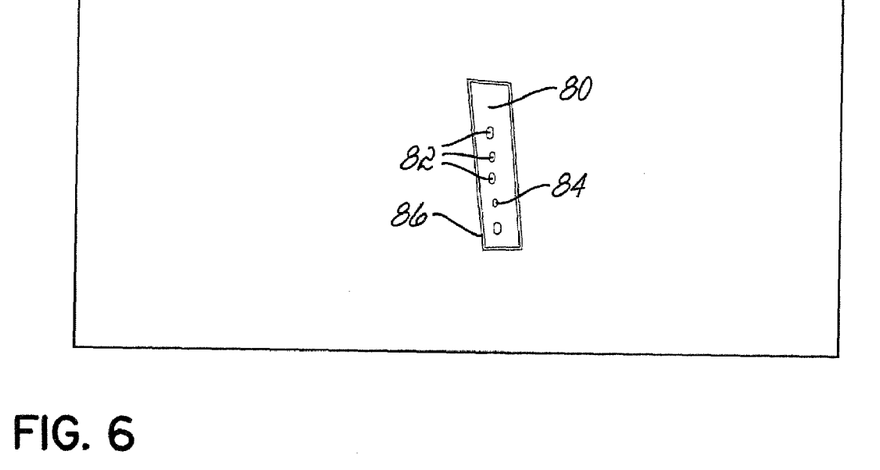
FIG. 6 is a representation of an image of infrared signatures for the group of features shown in FIGS. 1 and 2 when processed according to the process shown in FIG. 3.

Next, the control 48 determines, at 312, a classification or qualitative characteristic of a detected feature using Equations 6 and 7 below. First, with Equation 6, a comparison of the detected feature area, A, is made with a stored selected partial limit size. If a feature area is greater than or equal to a selected partial limit size, which is in a range of about 1-50 points, the feature is classified as a through hole 82 shown in FIG. 6; however, if the feature area is less than the partial limit size, the feature is classified as a partially blocked hole 84. The partial limit size is selected during the setup cycle. Using Equation 7, blocked holes 80 are determined by calculating a difference between an expected number of holes and a total number of holes detected. Extra holes are indicated to by a negative result of Equation 7.

$$A = \Sigma \text{feature\_points} \quad \text{(Eq. 6)}$$

$$E = \text{expected\_features} - \text{no\_features\_found} \quad \text{(Eq. 7)}$$

Thereafter, the control 48, at 314, determines whether all detected features in the feature array have been classified. If not, the classification process described above is repeated until all features in the feature array have been classified. Next, the control 48 determines, at 316, whether the current position and orientation of the IR camera is the last position and orientation. If not, the process of FIG. 3 is repeated until the IR camera 50 has been moved to all of the positions and orientations stored in the memory 78 and thus inspecting and classifying all of the blade features 22.

In order to establish desired positions and orientations for the IR camera 50 and determine values for many of the parameters used in executing the inspection cycle program 92 of FIG. 3, a setup cycle process is executed. In a first step of the setup cycle, the robotic arm 46 is moved to various preliminary positions around the blade 20 by an operator providing input commands to the control 48. At each preliminary position, an IR setup image is taken and stored in the computer 48; and a sufficient number of preliminary positions are chosen, so that all of the blade features 22 to be inspected are in one or more setup images. Further, to provide the most reliable feature discrimination, at each of the preliminary positions, the IR camera 50 is oriented such that the centerline of the lens 51 is generally parallel to a centerline of the features or holes 22 to be inspected. However, the feature inspection systems and processes described herein are operable with other IR camera orientations.

Next, for convenience, often the setup images are transferred to a computer remote from the control 48 of the inspection system 38 in order to finish the setup process. Such a remote computer is loaded with the inspection cycle program of FIG. 3 and is able to operate the inspection cycle program in a simulation mode. Further, the user is able to create a display of each of the setup images using a known program that converts the X-Y temperature point grid pattern of each image to a color or gray scale. Upon viewing each image, the user determines which, if any, features are best shown in that image. In that viewing process, the inspection cycle program of FIG. 3 is executed using default values for setup selectable parameters, for example, the target size setting, the temperature array index, the temperature threshold, the partial limit size and other parameters.

The user is able to change the values of those parameters and observe how the result of the inspection cycle program changes in terms of being able to better discriminate, identify and classify one or more features of interest. The results of the inspection cycle program are displayed to the user in a manner similar to the view shown in FIG. 6. Thus, for example, during the simulation, the user can increase the target size setting to see if that impacts the resulting discrimination and classification. Further, the gas temperatures can be changed to increase the resulting temperature difference determined in Equation 3. Often the larger the temperature difference the better the discrimination and the faster the feature inspection process can be executed. However, gas temperatures that are too high or too low will affect feature discrimination, so there must a balance struck between a temperature difference and the gas temperatures.

If the user is not satisfied with the result of the simulation of the inspection cycle program, the setup image can be deleted; and the next setup image viewed. If the user is satisfied with the resulting feature classification of the inspection cycle program simulation, the user places a boundary around one or more of the features being observed, for example, the boundary 86 of FIG. 6. That boundary represents a region of interest in a setup image taken at a particular preliminary position and orientation. In any setup image, the user can create as many boundaries or regions of interest as there are holes; and each region of interest can include one or more holes or rows of holes. Further, that particular preliminary position and orientation is defined as a programmed position and orientation that are to be used during subsequent executions of the inspection cycle program either in a simulation mode or during a part inspection cycle or process.

The above process is repeated until all of the features 22 on the blade 20 have been inspected in a region of interest. If some features cannot be adequately defined, then more setup images must be taken; and the above process repeated for those features. At this point, the inspection cycle program 92 includes (1) all of the positions and orientations of the IR camera 50 that are necessary to inspect the desired blade features 22, (2) all of the regions of interest 86 for a position and orientation, wherein each region of interest defines one or more of the blade features, and (3) values for all of the selectable parameters, for example, the target size setting, the temperature array index, the temperature threshold, the partial limit size and other parameters, which have been determined to provide the best feature discrimination. The inspection cycle program is then transferred to the control memory 78, and an inspection cycle can be executed.

A pre-inspection cycle is used to normalize the temperature of the blade 20. In the pre-inspection cycle, the control 48 opens the valves 64, 52 to initiate flows of air and helium. Temperature feedback signals from the temperature sensors 70, 58 are used by the control 48 to operate the respective heater 68 and chiller 56 to bring the air and helium to a desired temperature. Further, the flows of cooled helium through the blade 20 and heated air over the blade skin 79 for a period of time, for example, 1-30 seconds, normalizes the temperature of the blade, that is, the blade temperature reaches a sufficiently stable value to permit execution of the inspection process.

During the pre-inspection cycle, the control 48 also operates the pressure regulators 72 and 60 to establish desired pressures for the heated air and chilled helium respectively. The desired pressures are chosen during the setup cycle to optimize a discrimination and classification of features in the IR image during the inspection process. For example, if the air is too cold or the helium is too hot, feature discrimination and classification will be adversely affected. Further, once desired pressures of the air and helium are established that provide an acceptable feature discrimination and classification, changes in the ambient pressure around the blade 20 will adversely affect the feature discrimination and classification process. Therefore, during the pre-inspection cycle, a pressure sensor 90 provides the control 48 with a pressure signal representing the ambient pressure around the blade 20. The control 48 then sets the desired air and helium pressures as respective multiple values of the ambient air pressure to establish a desired ratio of air and helium pressures. Further, as the ambient pressure changes during subsequent executions of the feature inspection program, the control 48 changes the respective multiple values to maintain the desired air and helium pressures in constant relationship with respect to the ambient air pressure. To determine the desired air and helium pressures, the robotic arm can be moved to different inspection programmed positions; and the IR camera images viewed. The air and helium pressures are then adjusted to obtain a desired quality of an IR image.

Figure 7:
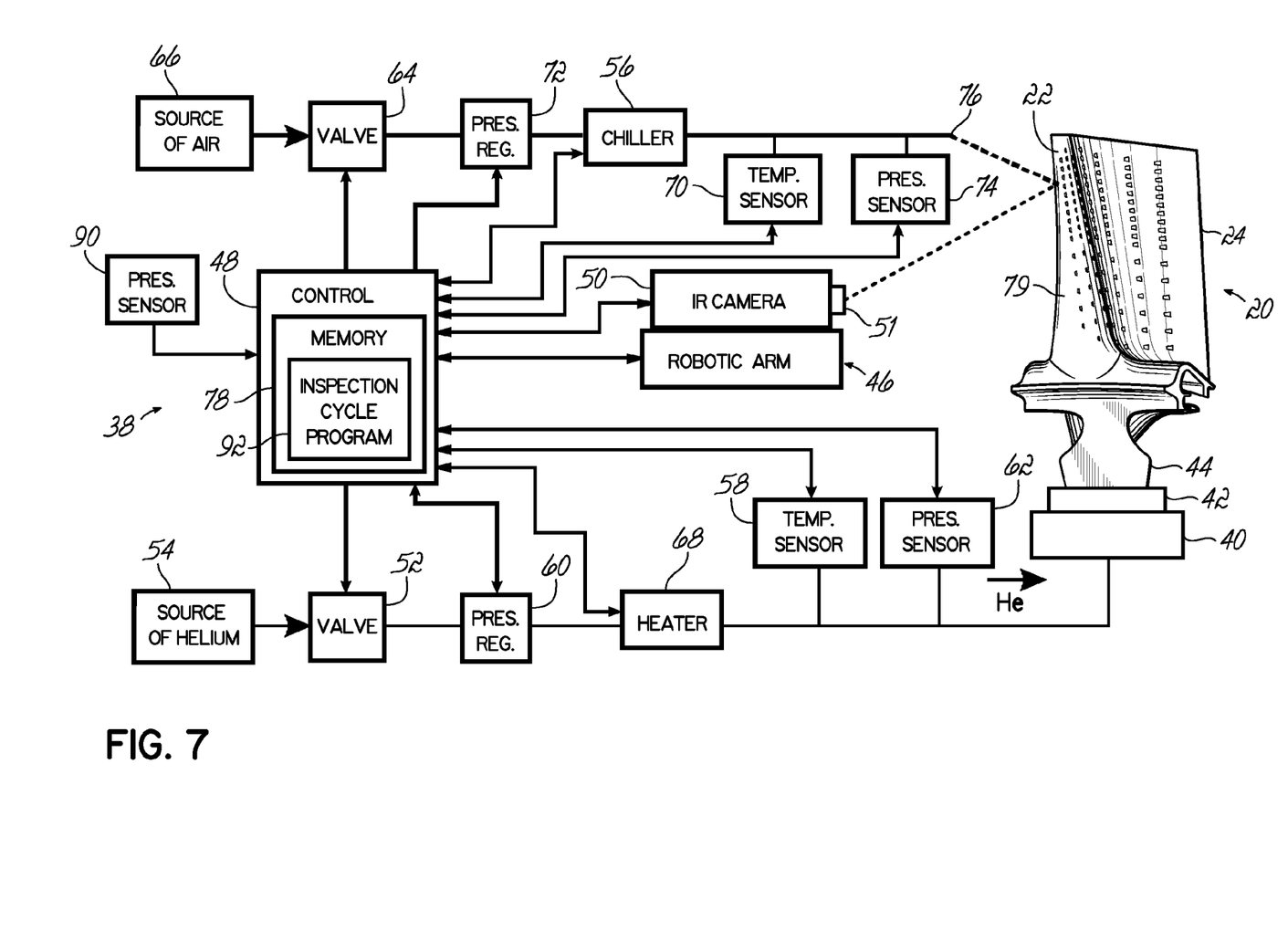
FIG. 7 is an overall schematic diagram of another exemplary embodiment of an automated inspection system for inspecting a complex feature fabricated in a part in accordance with the principles of the present invention.

In an alternative exemplary embodiment shown in FIG. 7, the feature inspection apparatus is changed by inverting the locations of the chiller 56 and the heater 68. With this embodiment, the control 48 operates the first pressure regulator 72 to supply air to the chiller 56 at a pressure in a range of about 0.05-3.0 PSIG. The chiller 56 cools the air to a temperature in a range of about 25-70 degrees. This cold air is applied through the nozzle 76 to an outer surface of the blade 20 around the various features being supplied the heated helium. At the same time, the control 48 operates the second pressure regulator 60 to supply the helium gas 54 to the heater 68 at a pressure in a range of about 0.1-35 PSIG. The heater 68 heats the helium gas to a temperature in a range of about 70-150 degrees, and the heated helium is applied to an interior cavity through an opening at the base 44 of the blade 20 and allowed to escape through the various features 22 to be inspected. After a period of time, the IR camera 50 is triggered to capture a temperature image; and the process previously described with respect to FIG. 3 is repeated to identify and classify various features. However, it should be noted that the Equation 3b is different from Equation 3a as indicated below:

The feature inspection systems 38 of FIGS. 1, 2 and 7 and method of FIG. 3 are substantially automated, faster, more error-free and less expensive than known tactile and visual inspection methods. The feature inspection systems 38 of FIGS. 1, 2 and 7 inject a gas through the internal passages of the blade 20, which is less dense and lighter than ambient air, for example, helium. The lighter gas provides a more predictable and reliable gas flow through the small passages within the blade 20 and out the complex shaped features 22 that exit on the blade skin 79. Further, the feature inspection systems 38 of FIGS. 1, 2 and 7 provide a simultaneous heating of one gas, for example, air, and cooling of the other gas, for example, helium. The simultaneous heating and cooling improves the capability of the feature inspection systems 38 to discriminate and classify features using the process described with respect to FIG. 3. In addition, the feature inspection systems of FIGS. 1, 2 and 7 continuously regulate the pressures of the gas with respect to ambient air pressure around the blade 20. Such a pressure regulation further improves the capability of the feature inspection systems 38 to discriminate and classify the blade features 22. Thus, the feature inspection systems 38 are especially useful for inspecting a large number of complex fabricated features, for example, cooling holes, in gas turbine component.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, while the hole inspection process described herein is directed to an application for inspecting features in a part, will be appreciated, the described hole inspection process can be used to inspect features on other parts, for example, fuel injectors, spray nozzles, combustors, stator blades, etc.

Therefore, the invention in its broadest aspects is not limited to the specific details shown and described. Consequently, departures may be made from the details described herein without departing from the spirit and scope of the claims which follow.

What is claimed is:

1. A feature inspection system for inspecting a feature extending from a cavity within a structure to an outer surface of the structure, the feature inspection system comprising:
    a first gas of a first density adapted to flow over the outer surface around the feature;
    a second gas of a second density different from the first density and adapted to flow into the cavity and through the feature;
    an infrared camera comprising a lens and adapted to provide a thermal image of an area of the outer surface around the feature, the thermal image comprising an array of elements representing a plurality of temperatures;
    a generally annular piece sized to fit around the lens, the annular piece comprising gas discharge passages spaced around a periphery of the annular piece and in fluid communication with the first gas for directing the first gas over the area of the outer surface; and
    a control in electrical communications with the infrared camera and causing the first gas and the second gas to simultaneously flow over the outer surface and through the feature, respectively, and the control processing the plurality of temperatures to identify a qualitative characteristic of the feature.

2. The feature inspection system of claim 1 wherein the second density is lower than the first density.

3. The feature inspection system of claim 1 wherein the first gas comprises air and the second gas comprises helium.

4. The feature inspection system of claim 1 wherein the gas discharge passages in the annular piece are angled toward a centerline of the annular piece.

5. A feature inspection system for inspecting a feature extending from a cavity within a structure to an outer surface of the structure, the feature inspection system comprising:
    a first gas adapted to flow over the outer surface around the feature;
    a first device for maintaining the first gas at a first temperature;
    a first pressure regulator for regulating a first pressure of the first gas;
    a second gas adapted to flow into the cavity and through the feature;
    a second device for maintaining the second gas at a second temperature different from the first temperature;
    a second pressure regulator for regulating a second pressure of the second gas;
    an infrared camera adapted to provide a thermal image of an area of the outer surface around the feature, the thermal image comprising an array of elements representing a plurality of temperatures; and
    a control in electrical communications with the infrared camera and causing the first gas at the higher temperature and the first pressure and the second gas at the lower temperature and the second pressure to simultaneously flow over the outer surface and through the feature, respectively, and the control processing the plurality of temperatures to identify a qualitative characteristic of the feature.

6. The feature inspection system of claim 5 wherein the first device is a heater for maintaining the first gas at a higher temperature and the second device is a chiller for maintaining the second gas at a lower temperature.

7. The feature inspection system of claim 5 wherein the first device is a chiller for maintaining the first gas at a lower temperature and the second device is a heater for maintaining the second gas at a higher temperature.

8. A feature inspection system for inspecting a feature extending from a cavity within a structure to an outer surface of the structure, the feature inspection system comprising:
    a first gas adapted to flow over the outer surface around the feature;
    a first pressure regulator for regulating a first pressure of the first gas;
    a second gas adapted to flow into the cavity and through feature;
    a second pressure regulator for regulating a second pressure of the second gas;
    a pressure sensor providing a pressure feedback signal representing an ambient pressure near the feature;
    an infrared camera adapted to provide a thermal image of an area of the outer surface around the opening of the feature, the thermal image comprising an array of elements representing a plurality of temperatures; and
    a control in electrical communications with the pressure sensor, the first and the second pressure regulators and the infrared camera, the control operating the first and the second pressure regulators to cause the first and the second pressures to maintain respective constant relationships with the ambient pressure, and the control processing the plurality of temperatures to identity a qualitative characteristic of the feature.

9. A feature inspection system for inspecting a feature extending from a cavity within a structure to an outer surface of the structure, the feature inspection system comprising:
a first gas of a first density adapted to flow over the outer surface around the feature;
a first device for maintaining the first gas at a first temperature;
a first pressure regulator for regulating a first pressure of the first gas;
a second gas of a second density different than the first density and adapted to flow into the cavity and through the feature;
a second device for maintaining the second gas at a second temperature different from the first temperature;
a second pressure regulator for regulating a second pressure of the second gas;
a pressure sensor providing a pressure feedback signal representing an ambient pressure near the feature;
an infrared camera adapted to provide a thermal image of an area of the outer surface around the feature, the thermal image comprising an array of elements representing a plurality of temperatures; and
a control in electrical communications with the first and the second devices, the first and the second pressure regulators, the pressure sensor and the infrared camera and causing the first gas and the second gas to simultaneously flow over the outer surface and through the feature, respectively, and the control processing the plurality of temperatures to identify a qualitative characteristic of the feature.

10. The feature inspection system of claim 9 wherein the feature is a plurality of holes and the feature characteristic is one of a good hole, an absence of a hole and a partially blocked hole.

11. A method of inspecting a feature extending from a cavity within a structure to an outer surface of the structure, the method comprising:
flowing a first gas at a first regulated pressure over the outer surface around the feature;
simultaneously flowing a second gas at a second regulated pressure and of a different density than the first gas into the cavity to flow through the feature;
generating a thermal image of the outer surface around the feature in response to the simultaneous flowing of the first gas and the second gas; and
processing the thermal image to identify a qualitative characteristic of the feature.

12. The method of claim 11 wherein the second gas is less dense than the first gas.

13. The method of claim 11 wherein the second gas is helium and the first gas is air.

14. A method of inspecting a feature extending from a cavity within a structure to an outer surface of the structure, the method comprising:
flowing a first gas of a first regulated pressure and a first temperature over the outer surface around the feature;
simultaneously flowing a second gas of a second regulated pressure and a second different temperature into the cavity to flow through the feature;
generating a thermal image of the outer surface around the feature in response to the simultaneous flowing of the first gas and the second gas; and
processing the thermal image to identify a qualitative characteristic of the feature.

15. The method of claim 14 wherein the first temperature is higher than the second temperature.

16. The method of claim 14 wherein the first temperature is lower than the second temperature.

17. A method of inspecting a feature extending from a cavity within a structure to an outer surface of the structure, the method comprising:
flowing a first gas of a first pressure over the outer surface around the feature;
simultaneously flowing a second gas of a second pressure into the cavity to flow through the feature;
determining an ambient pressure around the feature;
maintaining the first pressure and the second pressure at respective constant relationships with respect to the ambient pressure;
generating a thermal image of the outer surface around the feature in response to the simultaneous flowing of the first gas and the second gas; and
processing the thermal image to identify a qualitative characteristic of the feature.

18. A method of inspecting a feature extending from a cavity within a structure to an outer surface of the structure, the method comprising:
flowing a first gas of a first density, a first pressure and a first temperature over the outer surface around the feature;
simultaneously flowing a second gas of a second different density, a second different pressure and a second different temperature into the cavity to flow through the feature;
determining an ambient pressure around the feature;
maintaining the first pressure and the second pressure at respective constant relationships with respect to the ambient pressure;
generating a thermal image of the outer surface around the feature in response to the simultaneous flowing of the first gas and the second gas; and
processing the thermal image to identify a qualitative characteristic of the feature.

19. The method of claim 18 wherein the feature is a plurality of holes and the characteristic feature is one of a good hole, an absence of a hole and a partially blocked hole.

20. An apparatus for inspecting features extending from a cavity within a structure to an outer surface of the structure, the apparatus comprising:
a thermal imaging device comprising a lens;
a positioning system for supporting the thermal imaging device and operable to position the lens at a desired position and orientation with respect to one of the features;
a source of a pressure regulated first gas;
a heater receiving the first gas and providing a flow heated gas;
a heating component supported by the positioning system and in fluid communication with the heated gas, the heating component being operable to heat an area of the outer surface around the one of the features;
a source of a pressure regulated second gas;
a chiller receiving the second gas and providing a flow of cooled gas into the cavity and to the one of the features;
a programmable control in electrical communications with the thermal imaging device, the positioning system, the heater and the chiller and operable to first heat the area of the outer surface around the one of the features and simultaneously cause the cooled gas to flow into the cavity, the control being further operable to cause the thermal imaging device to capture and save a thermal image of the area of the outer surface including the one of the features.

21. The apparatus of claim 20 wherein the heating component further comprises a plurality of nozzles mounted circumferentially around the lens of the thermal imaging device.

22. A method of inspecting features extending from a cavity within a structure to an outer surface of the structure, the method comprising:
 (a) positioning a thermal imaging device at a desired position and orientation with respect to one of the features;
 (b) heating an area of the outer surface including the one of the features with a pressure regulated flow of a first gas;
 (c) simultaneously providing a flow of a pressure regulated cooled gas into the cavity to the one of the features;
 (d) capturing a thermal image of the area of the outer surface including the one of the features;
 (e) saving the thermal image; and
 (f) iterating steps (a)-(e) for others of the features.

23. The method of claim 22 wherein the heated gas is air and the cooled gas is helium.

24. The method of claim 22 wherein the method further comprises analyzing the thermal image to identify a qualitative characteristic of the one of the feature.

* * * * *

UNITED STATES PATENT AND TRADEMARK OFFICE
CERTIFICATE OF CORRECTION

| | | |
|---|---|---|
| PATENT NO. | : 7,388,204 B2 | Page 1 of 2 |
| APPLICATION NO. | : 11/424084 | |
| DATED | : June 17, 2008 | |
| INVENTOR(S) | : Douglas E. Key and Beau Easton | |

It is certified that error appears in the above-identified patent and that said Letters Patent is hereby corrected as shown below:

Title Page

Insert the heading ---Related U.S. Application Data--- before the heading "(51) Int. Cl.".

First column, insert after the heading "Related U.S. Application Data"
---The present application claims the filing benefit of U.S. Provisional Application Serial No. 60/748,020, filed December 7, 2005.---.

In the Specification

Column 1

Line 23, "and, to extend the useful life of," should be ---and to extend the useful life of---.

Column 2

Line 32, "thus, removes" should be ---thus removes---.

Column 3

Line 65, "and thus," should be ---and thus---.

Signed and Sealed this
Fourteenth Day of October, 2014

Michelle K. Lee
*Deputy Director of the United States Patent and Trademark Office*

Column 4

Line 20, "control memory 76" should be ---control memory 78---.

Line 31, "for total of" should be ---for a total of---.

Column 5

Line 12, "n-" should be --- n=---.

Column 7

Line 41, "so there must a" should be ---so there must be a---.

Line 55, "orientation is defined" should be ---orientation are defined---.

Column 9

Line 3, after "indicated below:", insert, $$\Delta temp = \overline{hole} - \overline{skin} \quad (\text{Eq. 3b})$$

Line 27, "in gas turbine" should be ---in a gas turbine---.

Line 36, "will be appreciated" should be ---it will be appreciated---.

Column 10

Lines 53-54, "through feature" should be ---through the feature---.

Column 12

Line 52, "flow heated" should be ---flow of heated---.

Column 14

Line 12, "feature" should be ---features---.